(12) United States Patent
Song et al.

(10) Patent No.: US 11,578,361 B2
(45) Date of Patent: Feb. 14, 2023

(54) GENE DETECTION METHOD, GENE DETECTION KIT AND GENE DETECTION DEVICE

(71) Applicant: HANGZHOU LIFEREAL BIOTECHNOLOGY CO., LTD., Hangzhou (CN)

(72) Inventors: Qian Song, Hangzhou (CN); Wenfei Xu, Hangzhou (CN); Xin Wang, Hangzhou (CN); Xiangzhao Zheng, Hangzhou (CN)

(73) Assignee: HANGZHOU LIFEREAL BIOTECHNOLOGY CO., LTD., Hangzhou (CN)

( * ) Notice: Subject to any disclaimer, the term of this patent is extended or adjusted under 35 U.S.C. 154(b) by 571 days.

(21) Appl. No.: 16/487,105

(22) PCT Filed: Jun. 6, 2018

(86) PCT No.: PCT/CN2018/090026
§ 371 (c)(1),
(2) Date: Aug. 20, 2019

(87) PCT Pub. No.: WO2018/223973
PCT Pub. Date: Dec. 13, 2018

(65) Prior Publication Data
US 2019/0376121 A1    Dec. 12, 2019

(30) Foreign Application Priority Data
Jun. 8, 2017   (CN) .......................... 201710429121.1

(51) Int. Cl.
*C12Q 1/686* (2018.01)
*B01L 3/00* (2006.01)
*B01L 7/04* (2010.01)

(52) U.S. Cl.
CPC .............. *C12Q 1/686* (2013.01); *B01L 3/508* (2013.01); *B01L 7/04* (2013.01);
(Continued)

(58) Field of Classification Search
CPC ......................... C12Q 1/6806; C12N 15/1003
See application file for complete search history.

(56) References Cited

U.S. PATENT DOCUMENTS

| | | | |
|---|---|---|---|
| 2005/0221281 A1 | 10/2005 | Ho | |
| 2007/0111303 A1* | 5/2007 | Inoue | ............... B01L 3/0268 |
| | | | 435/288.5 |
| 2013/0136671 A1* | 5/2013 | Li | ........................ B01L 3/52 |
| | | | 422/522 |

FOREIGN PATENT DOCUMENTS

| | | |
|---|---|---|
| CN | 101149376 A | 3/2008 |
| CN | 104673625 A | 6/2015 |

(Continued)

OTHER PUBLICATIONS

Written Opinion of Japanese Patent Application 2019-565606, dated Jul. 27, pp. 1-4 (Year: 2021).*
(Continued)

*Primary Examiner* — Young J Kim
(74) *Attorney, Agent, or Firm* — Bayramoglu Law Offices LLC

(57) ABSTRACT

A gene detection method, a gene detection kit, and a gene detection device, including the following steps: providing a plurality of separation cavities on a kit, using a plunger to separate adjacent separation cavities, and respectively providing a lysate solution, a washing solution and a reaction solution in the separation cavities; when detecting a sample, pushing each plunger to align a plunger hole of the plunger with the separation cavity, thereby making the separation cavities interconnected; then, controlling magnetic beads in the kit to drive the sample to be tested to pass through the (Continued)

separation cavities in sequence by an electromagnetic control method, carrying out a lysing, a washing and a reaction in sequence; and finally, performing a optical detection on a gene in the reaction solution from outside.

2 Claims, 5 Drawing Sheets

(52) U.S. Cl.
CPC ............... *B01L 2300/0654* (2013.01); *B01L 2300/1883* (2013.01); *B01L 2400/043* (2013.01)

(56) References Cited

FOREIGN PATENT DOCUMENTS

| | | | |
|---|---|---|---|
| CN | 105349530 A | * | 2/2016 |
| CN | 105349530 A | | 2/2016 |
| CN | 107151700 A | | 9/2017 |
| EP | 1469068 A1 | | 10/2004 |

OTHER PUBLICATIONS

English Translation of CN-105349530-A (via google patent), retrieved on-line, retrieved from: https://patents-google-com.translate.goog/patent/CN105349530A/zh?_x_tr_sl=auto&_x_tr_tl=en&_x_tr_hl=en-US&_x_tr_pto=nui; retrieval date: Nov. 13, pp. 1-6. (Year: 2021).*

* cited by examiner

GENE DETECTION METHOD, GENE DETECTION KIT AND GENE DETECTION DEVICE

CROSS REFERENCE TO THE RELATED APPLICATIONS

This application is the national phase entry of International Application No. PCT/CN2018/090026, filed on Jun. 6, 2018, which is based upon and claims priority to Chinese Patent Application No. 201710429121.1, filed on Jun. 8, 2017, the entire contents of which are incorporated herein by reference.

TECHNICAL FIELD

The present invention relates to a gene detection method, a gene detection kit and a gene detection device, and belongs to the technical field of medical detection.

BACKGROUND

Gene detection is a technique for detecting deoxyribonucleic acid (DNA) by blood, other body fluids, or cells, namely, taking detached oral mucosal cells or other tissue cells of a person, amplifying gene information thereof, and then detecting the DNA molecular information in the cells of the person by a specific device, so as to predict a risk of a disease, and analyze conditions of various genes contained therein, thereby enabling the person to know his gene information, and therefore avoiding or delaying the occurrence of the disease by improving his living environment and living habits.

Gene detection can diagnose diseases, and can be used to predict disease risk as well. Disease diagnosis is achieved by using gene detection techniques to detect mutated genes that cause hereditary diseases. The most commonly used gene detection is genetic disease detection for newborns, genetic disease diagnosis and auxiliary diagnosis of some common diseases. Currently, more than 1,000 genetic diseases can be diagnosed by gene detection techniques.

Since biological tissue cells are commonly used as a sample in the gene detection, steps of lysing, washing, and amplifying the cells are required in the gene detection, followed by detecting genes by an optical detection. Different treatments are involved in the various steps, and the sample usually needs to be processed by multiple devices respectively for the different steps, so the detection is complicated. Moreover, when performing the different steps, sometimes it is necessary to transfer the sample to a different carrier, which is likely to pollute the sample and affect the detection accuracy.

SUMMARY

The present invention aims to provide a gene detection method, a gene detection kit and a gene detection device. A process of a gene detection can be simplified, and all steps of the gene detection can be completed in one device, thereby not only preventing the gene detection from relying on a large number of devices, improving a detection efficiency, but also avoiding a pollution introduced in a detection process, improving a detection accuracy.

Technical solution of the present invention: a gene detection method, including: providing a plurality of separation cavities on a kit, using a plunger to separate adjacent separation cavities, and respectively providing a lysate solution, a washing solution and a reaction solution in the separation cavities; when detecting a sample, pushing each plunger to align a plunger hole of the plunger with the separation cavity, thereby making the various separation cavities interconnected; then, controlling magnetic beads in the kit to drive the sample to be tested to pass through the each separation cavity in sequence by an electromagnetic control method, carrying out a lysing, a washing and a reaction in sequence; and finally, performing an optical detection on a gene in the reaction solution from outside.

In the above gene detection method, the reaction is a polymerase chain reaction (PCR) or an isothermal amplification reaction, an enzyme required for the reaction is provided in the plunger hole of the plunger, and when the plunger hole of the plunger is aligned with the separation cavity, the enzyme automatically falls into the reaction solution due to a gravity of the enzyme.

In the above gene detection method, a detection portion of the optical detection is located at a bottom of the separation cavity containing the reaction solution, and the bottom of the separation cavity containing the reaction solution is provided with a concave portion toward an outside of the kit. During a detection, the kit is in an inclined state, and the concave portion of the separation cavity containing the reaction solution faces downward, and the magnetic beads in the reaction solution are automatically concealed in the concave portion to avoid an interference in the optical detection.

A gene detection kit for realizing the above method, including a box body with a flip lid at a top, wherein, a lysing section and a washing section separated by a plunger are respectively provided in the box body from top to bottom, and a reaction section is provided below the washing section, at least one washing section is provided, the plunger is provided horizontally, and a plunger hole in a vertical direction is provided in the plunger; the lysing section is provided with a lysing solution, and the lysing solution is internally provided with ferromagnetic mixing balls and magnetic beads capable of passing through the plunger hole; the washing section is provided with a washing solution; and the reaction section is provided with a reaction solution.

In the above gene detection kit, a steel tube coated with an enzyme is provided in the plunger hole of the plunger between the washing section and the reaction section.

In the above gene detection kit, a spring is provided at an end of the plunger, an ejector rod protruding outside the box body is connected to the other end of the plunger; and a slope is provided at a lower side of an outer end of the ejector rod.

In the above gene detection kit, the reaction section is located in the box body, and a hidden section recessed toward an outside of the box body is provided at a bottom of the reaction section.

In the above gene detection kit, the plunger hole has a taper of 3°-5° and a center diameter of 3-5 mm. Such a setting not only facilitates a passage of the magnetic beads, but also interrupts a free passage of solutions in various sections by a capillary action.

A bottom end of the lysing section is configured as a narrow-necked opening having a wide top and a narrow bottom, and each side of the narrow-necked opening is in an included angle of 25°-35° with a vertical direction to facilitate a sufficient lysing and a smooth gathering of the magnetic beads into the plunger hole.

In the above gene detection kit, the washing section may also be provided outside the box body, and the washing section is configured to be a thin-walled transparent cone-shaped tube.

A gene detection device for implementing the above method, including a kit holding tank, wherein, an electromagnetic coil array composed of a plurality of electromagnetic coils is provided at one side of the kit holding tank, and a plurality of heating aluminum blocks closely attached to the kit holding tank are provided at an other side of the kit holding tank, and a refrigerating fin is provided on each of the heating aluminum blocks; a detecting optical fiber having a top end directly facing a tank bottom is provided at the tank bottom of the kit holding tank, and the detecting optical fiber is connected to an optical detection module.

In the above gene detection device, an occulting bar in a depth direction of the tank is provided in the kit holding tank, during a process of inserting the kit into the kit holding tank, the occulting bar sequentially pushes each plunger of the kit to move, thereby making all the separation cavities interconnected in the kit.

In the above gene detection device, the kit holding tank is provided obliquely at an included angle of 30° to 60° with a vertical direction.

In the above gene detection device, the electromagnetic coil array includes a mixing array and a dragging array, the mixing array includes a plurality of electromagnetic coils arranged in an annular distribution and close to a position of an opening of the kit holding tank, and the dragging array includes a plurality of electromagnetic coils linearly arranged from the mixing array to the bottom of the kit holding tank.

In the above gene detection device, the electromagnetic coils of the dragging array are divided into two rows including a left row and a right row, any one electromagnetic coil one of the two rows is opposite to a space between two adjacent electromagnetic coils of the other one of the two rows.

In the above gene detection device, a heat dissipating aluminum block is provided on the electromagnetic coil array, and a heat dissipating fin is provided on the refrigerating fin.

Compared with the prior art, the present invention utilizes a plunger to separate a plurality of sections (cavities) in a kit. The lysate solution, the washing solution and the reaction solution can be separately placed in the sections, so that the multiple steps of the gene detection can be carried out in the same kit (using one device), which is not prone to cause secondary pollution, greatly improves the work efficiency and the detection accuracy, and can solve the problem that the gene detection requires a lot of supporting devices. In the present invention, the plunger is used for separation, therefore various sections can be interconnected by a simple mechanical action without any other treatment (If paraffin or other substances are used for separation, heating is required during interconnection and assembly, and the heating will affect reagents and samples in the kit, thereby affecting the detection accuracy). It is more convenient to operate, and the assembly of the plunger is easier, which facilitates the assembly of the reagents in various sections.

Figure 1:
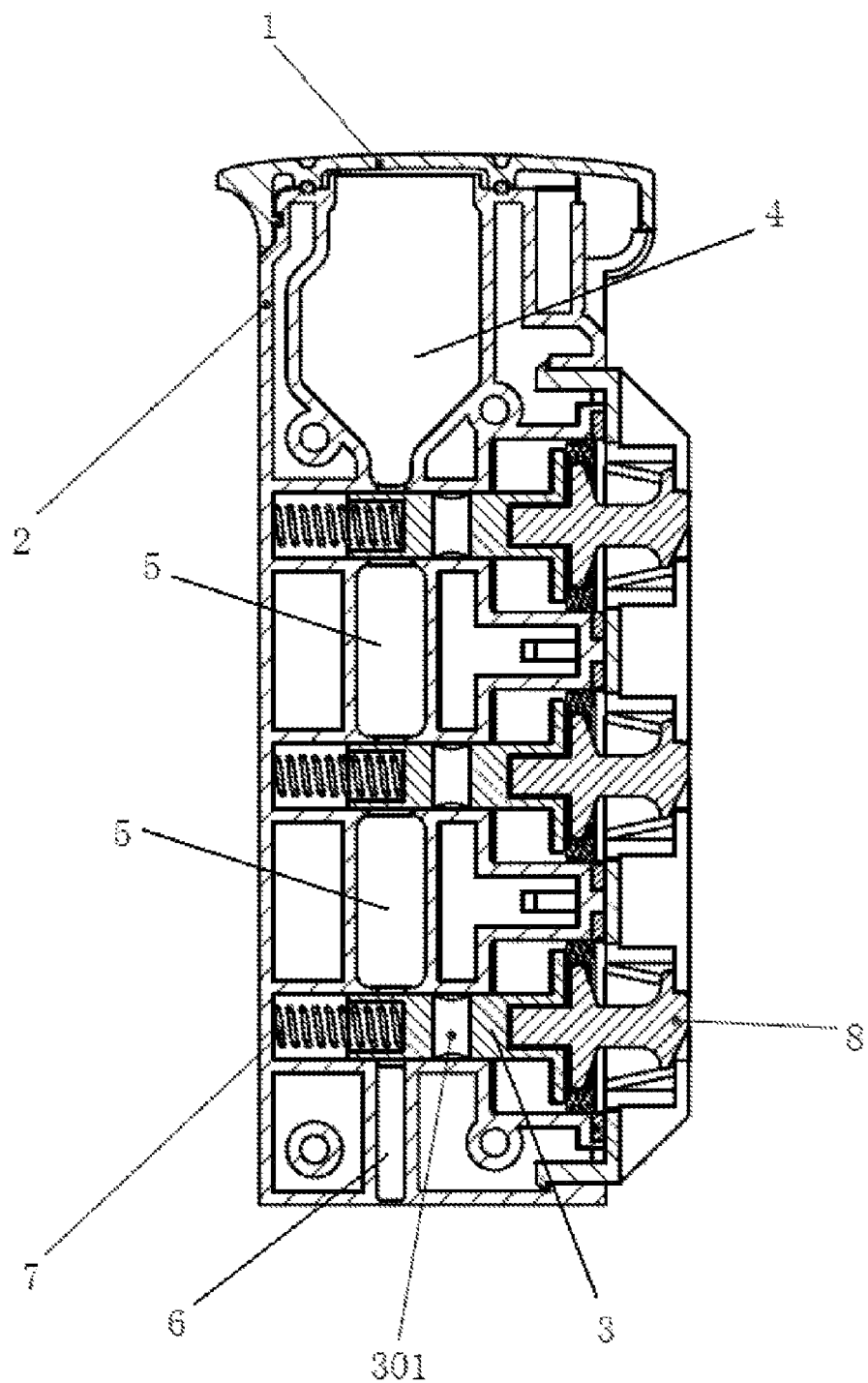
FIG. 1 is structural schematic diagram of a kit according to the present invention.

Reference numerals in the figures are described below: 1—flip lid, 2—box body, 3—plunger, 301—plunger hole, 4—lysing section, 5—washing section, 6—reaction section, 7—spring, 8—ejector rod, 9—kit holding tank, 10—electromagnetic coil array, 11—refrigerating fin, 12—detecting optical fiber, 13—occulting bar, 14—heat dissipating aluminum block, 15—heat dissipating fin, 16—heating aluminium block, 101—mixing array, 102—dragging array, and 601—hidden section.

DETAILED DESCRIPTION OF THE EMBODIMENTS

The present invention will be further described in reference with the drawings and embodiments, which are not used as a basis for limitation of the present invention.

Embodiment

A gene detection method includes the following steps: providing a plurality of separation cavities in a kit, using a plunger to separate adjacent separation cavities, and respectively providing a lysate solution, a washing solution and a reaction solution in the separation cavities; when detecting a sample, pushing each plunger to align a plunger hole of the plunger with the separation cavity, thereby making the separation cavities interconnected; then, controlling magnetic beads in the kit to drive the sample to be tested to pass through the separation cavities in sequence by an electromagnetic control method, carrying out a lysing, a washing and a reaction in sequence; and finally, performing a optical detection on a gene in the reaction solution from outside. The reaction is a polymerase chain reaction (PCR) or an isothermal amplification reaction, an enzyme required for the reaction is provided in the plunger hole of the plunger, and when the plunger hole of the plunger is aligned with the separation cavity, the enzyme automatically falls into the reaction solution due to a gravity of the enzyme. A detection portion of the optical detection is located at a bottom of the separation cavity containing the reaction solution, and the bottom of the separation cavity containing the reaction solution is provided with a concave portion toward an outside of the kit. During a detection, the kit is in an inclined state, and the concave portion of the separation cavity containing the reaction solution faces downward, and the magnetic beads in the reaction solution are automatically concealed in the concave portion to avoid an interference in the optical detection.

Figure 2:
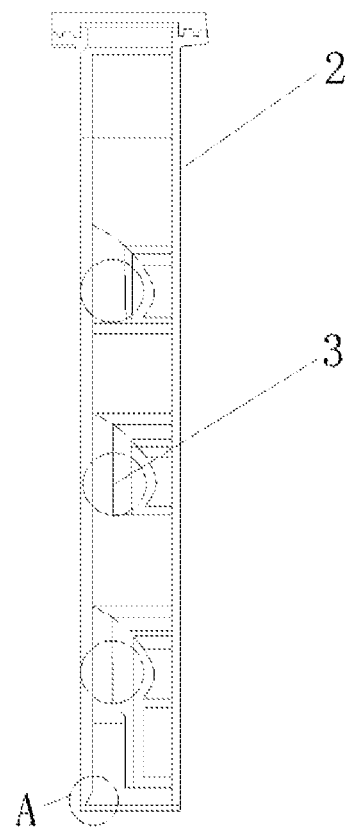
FIG. 2 is a side view of FIG. 1.
Figure 3:
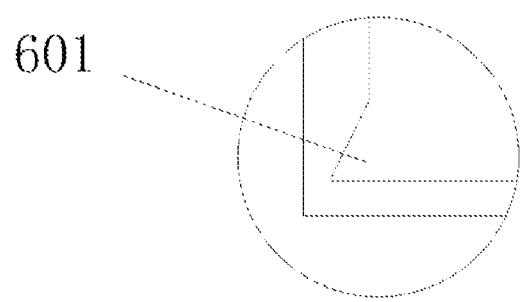
FIG. 3 is an enlarged view of a portion A of FIG. 2.

A gene detection kit for realizing the above method, as shown in FIGS. 1-3, includes the box body 2 with the flip lid 1 at the top, wherein, the lysing section 4, the washing section 5, and the reaction section 6 separated by the plunger 3 are respectively provided in the box body 2 from top to bottom, the plunger 3 is provided horizontally, and the plunger hole 301 in a vertical direction is provided in the plunger 3; the lysing section 4 is provided with the lysing solution, and the lysing solution is internally provided with ferromagnetic mixing balls and magnetic beads capable of passing through the plunger hole 301; the washing section 5 is provided with the washing solution; and the reaction section 6 is provided with the reaction solution. A steel tube coated with an enzyme is provided in the plunger hole 301 of the plunger 3 between the washing section 5 and the reaction section 6. The spring 7 is provided at an end of the plunger 3, the ejector rod 8 protruding outside the box body 2 is connected to the other end of the plunger 3; and a slope is provided at a lower side of an outer end of the ejector rod 8. The hidden section 601 recessed toward an outside of the box body 2 is provided at a bottom of the reaction section 6. The plunger hole 301 has a taper of 3°-5° (preferably 4°) and a center diameter of 3-5 mm (preferably 4 mm). A bottom end of the lysing section 4 is configured as a narrow-necked opening having a wide top and a narrow bottom, and each side of the narrow-necked opening is at an included angle of 25°-35° (preferably 30°) with a vertical direction.

Figure 8:
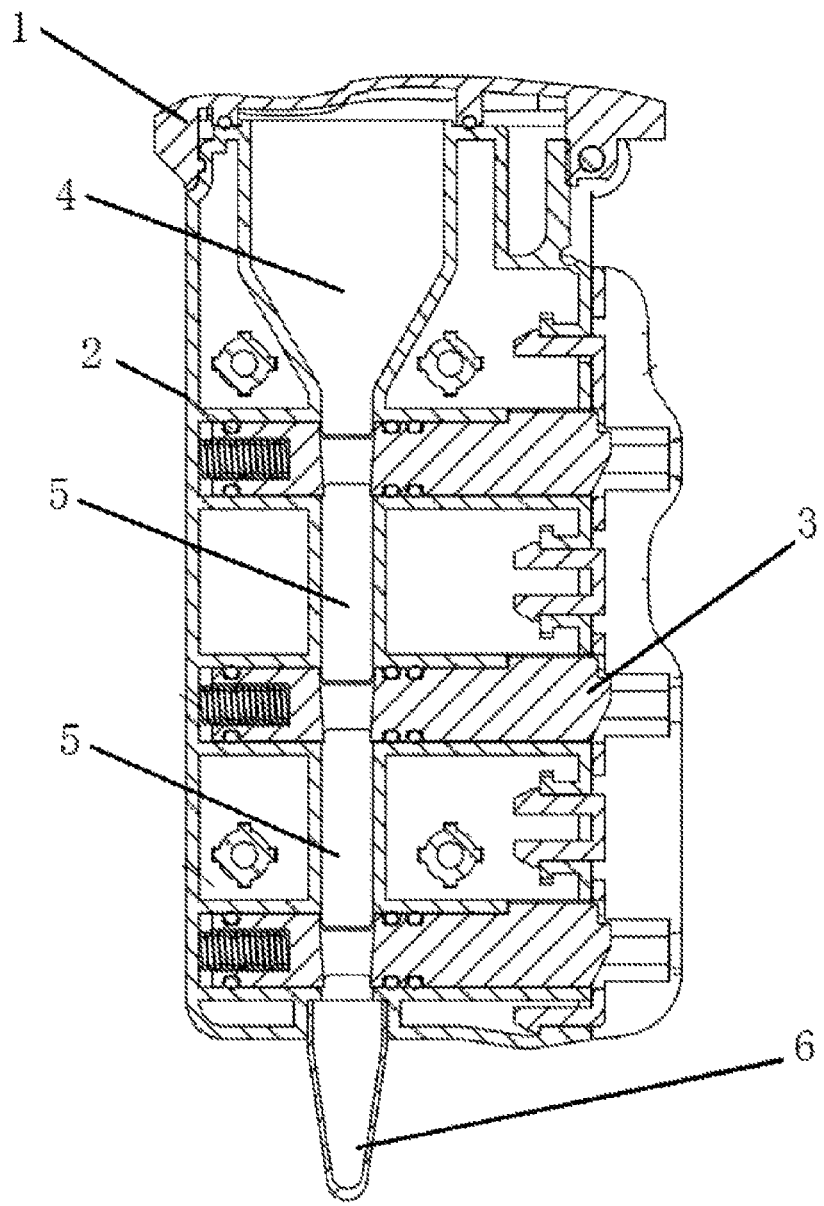
FIG. 8 is a structural schematic diagram a kit using a thin-walled transparent cone-shaped tube as a washing section.

In addition, the washing section 5 may also be in a form of thin-walled transparent cone-shaped tube and provided outside the box body 2 (as shown in FIG. 8) for the final optical detection. During a detection, a light probe is used to align a bottom or a side wall of the thin-walled transparent cone-shaped tube, and the electromagnetic coils are used to attract the magnetic beads to other places.

Figure 4:
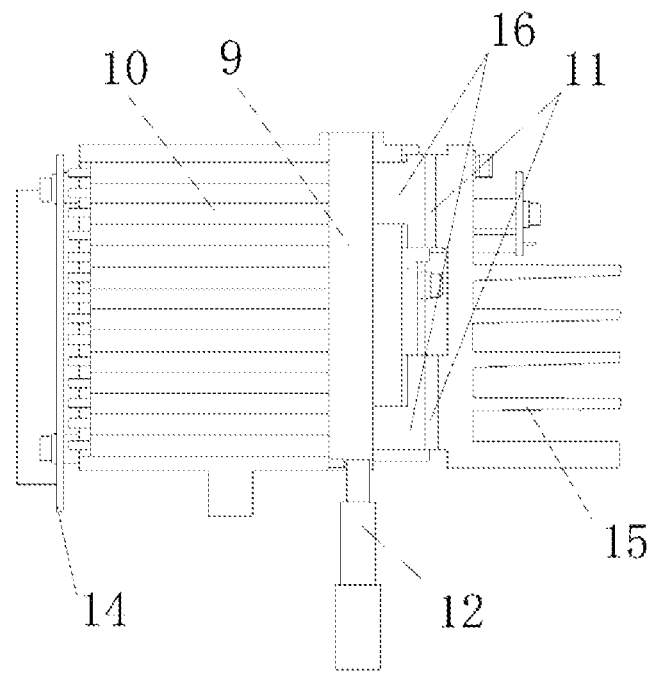
FIG. 4 is a structural schematic diagram of a detection device according to the present invention.

A gene detection device for implementing the above method, as shown in FIG. 4, includes the kit holding tank 9, wherein, the electromagnetic coil array 10 composed of a plurality of electromagnetic coils is provided at one side of the kit holding tank 9, and a plurality of heating aluminum blocks 16 closely attached to the kit holding tank 9 are provided at an other side of the kit holding tank, and the refrigerating fin 11 is provided on each of the heating aluminum blocks 16; the detecting optical fiber 12 having a top end directly facing a tank bottom is provided at the tank bottom of the kit holding tank 9, and the detecting optical fiber 12 is connected to an optical detection module.

Figure 5:
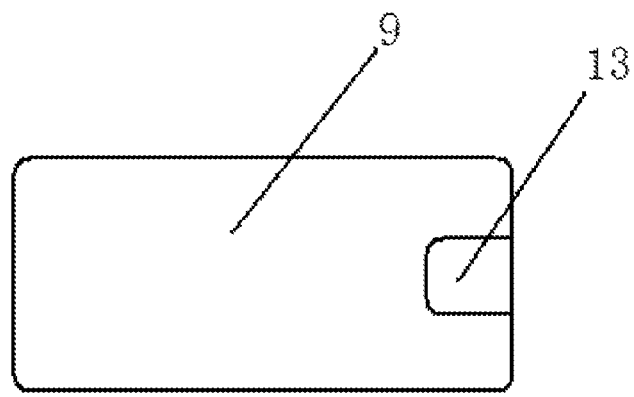
FIG. 5 is a schematic diagram showing an internal structure of a kit holding tank.

The occulting bar 13 in a depth direction of the tank is provided in the kit holding tank 9, during a process of inserting the kit into the kit holding tank 9, the occulting bar 13 sequentially pushes each plunger of the kit to move, thereby making all the separation cavities interconnected in the kit. An internal structure of the kit holding tank 9 is shown in FIG. 5.

The kit holding tank 9 is provided obliquely at an included angle of 30° to 60° (preferably 50°) with the vertical direction.

Figure 6:
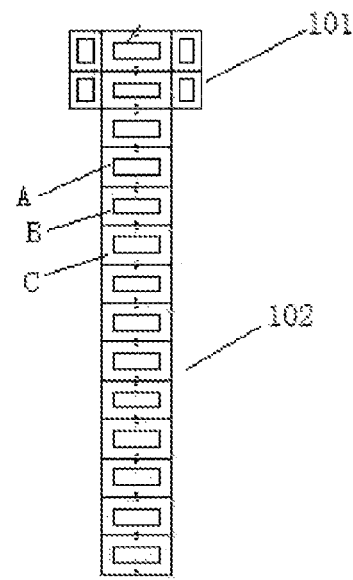
FIG. 6 is a structural schematic diagram of a single-row electromagnetic coil array.
Figure 7:
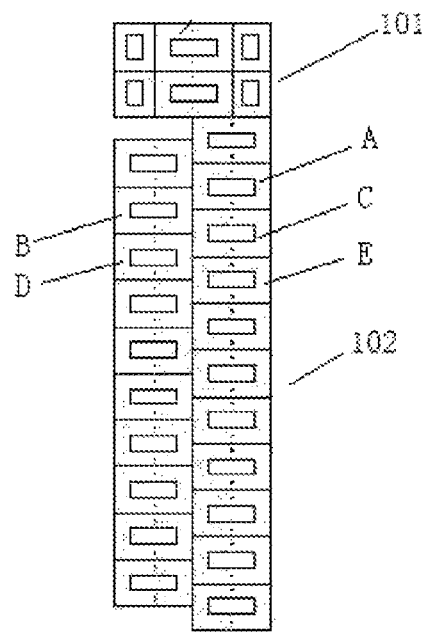
FIG. 7 is a structural schematic diagram of a double-row electromagnetic coil array.

The electromagnetic coil array 10 includes the mixing array 101 and the dragging array 102, the mixing array 101 includes a plurality of electromagnetic coils arranged in an annular distribution and close to a position of an opening of the kit holding tank 9. The dragging array 102 includes a plurality of electromagnetic coils linearly arranged from the mixing array 101 to the bottom of the kit holding tank 9. The dragging array 102 may be a single-row array, as shown in FIG. 6, or be a double-row array, as shown in FIG. 7. The electromagnetic coils of the dragging array 102 are divided into two rows including a left row and a right row, any one electromagnetic coil of one of the two rows is opposite to a space between two adjacent electromagnetic coils of the other one of the two rows. The heat dissipating aluminum block 14 is provided on the electromagnetic coil array 10, and a heat dissipating fin 15 is provided on the refrigerating fin 11.

Each of the electromagnetic coils 1 in the mixing array 101 sequentially completes an on/off process in a clockwise or counterclockwise direction, which is circulated for a plurality of times. Alternatively, each of the electromagnetic coils 1 in the mixing array 101 completes the on/off process in a shape of "8" in sequence, which is circulated for a plurality of times. The latter has a better mixing effect, and test shows that the latter used for sample lysing has a higher lysing efficiency.

When the dragging array 102 is a single-row array, each of the electromagnetic coils 1 in the dragging array 102 can be operated in a single on/off method after the mixing array 101 stops running. For example, A is turned on; then A is turned off, and B is turned on; then B is turned off, and C is turned on; and then C is turned off, and so on.

A mode of simultaneously controlling two sites as a group may also be used. For example, A and B are turned on simultaneously, then A and B are turned off, and B and C are turned on; and so on. Alternatively, B is turned on after a period of time when A is turned on, and A is turned off after a period of time when A and B are turned on simultaneously; C is turned on after a period of time when B is turned on singly, and B is turned off after a period of time when B and C are turned on simultaneously, and so on. The experiment shows that the nano-magnetic beads are dragged more smoothly by this method, and a success rate of dragging the magnetic beads exceeds 95%.

When the dragging array 102 is a double-row array, each of the electromagnetic coils 1 in the dragging array 102 may be controlled in the mode of controlling two sites as a group after the mixing array 101 stops running. For example, A and B are turned on simultaneously, then A and B are turned off, and B and C are turned on; and so on.

A mode of controlling three sites as a group may also be used. For example, A, B, and C are turned on simultaneously; then A, B, and C are turned off, and B, C, and D are turned on; then B, C, and D are turned off, and C, D, and E are turned on, and so on.

In the mixing array, a magnetic core of the each electromagnetic coil is formed by closely arranging three pieces of silicon steel sheets of 0.65 mm×4 mm×60 mm, and six layers of enameled wires with a wire diameter of 0.25 mm (about 1200 coils) are winded outside the magnetic core. A magnetic core of the dragging array is formed by closely arranging three pieces of silicon steel sheets of 0.65 mm×6 mm×60 mm, and six layers of enameled wires with a wire diameter of 0.25 mm (about 1200 coils) are winded outside the magnetic core. Magnetic field strengths of the mixing array 101 and the dragging array 102 are measured to be about 2000 Gs and 2200 Gs respectively by a gaussmeter at 15 volts of electricity. A best dragging effect occurs when a distance between the electromagnetic coil and the magnetic beads is 1.3 mm, and the electromagnetic coil is not overheated. The on-off interval of the electromagnetic coils in the mixing array 101 is controllable, ranging from 15 ms to 500 ms. When the on-off interval of the electromagnetic coils in the mixing array 101 is controlled to range from 35 ms to 65 ms, the mixing effect is the best.

A specific application method of the kit and the detection device of the present invention is as follows:

1) A sample is put into the box body 2, and the flip lid 1 is covered. Then, the box body 2 is inserted into the kit holding tank 9 of the gene detection device. During the insertion process, the ejector rods 8 of the plungers 3 are sequentially pushed by the occulting bar 13, so that each plunger 3 is moved against an elastic force of the spring 7, causing the plunger hole 301 to be aligned with the separation cavity, thereby making the lysing section 4, the washing section 5 and the reaction section 6 interconnected.

2) The mixing array 101 of the electromagnetic coil array 10 is activated, and the electromagnetic coils of the mixing array 101 are sequentially turned on and off in a ring shape, and the ferromagnetic mixing balls vigorously agitate the lysing solution and the sample under a magnetic drive. The refrigerating fin 11 beside the lysing section is turned on simultaneously to control a lysing temperature.

3) The dragging array 102 of the electromagnetic coil array 10 is turned on, causing the electromagnetic coils of the dragging array 102 to be turned on and off sequentially from top to bottom, and the magnetic beads carry a lysed sample after cleaning by a cleaning solution, and finally enter the reaction solution, simultaneously, the steel tube carrying the enzyme in the plunger is taken into the reaction solution. The refrigerating fin 11 beside the reaction section is turned on to control a reaction temperature.

4) The electromagnetic coil array 10 is turned off, and the magnetic beads fall into the hidden section 601 due to their own gravity.

5) An optical signal is detected from a bottom of the box body by the detecting optical fiber 12.

6) A gene of the sample is analyzed based on the optical signal by the optical detection module.

A specific application embodiment of the kit is provided. An enzyme-linked immunoassay kit for group B *streptococcus* (GBS) includes a sample processing section separated by a plunger, two first washing sections, an antibody binding detection section, two second washing sections, a luminescent substrate binding section, two third washing sections, and a termination section. The plunger is provided with a plunger hole. The sample processing section is provided with a sample processing solution, and a metal stirrer and submicron superparamagnetic immunomagnetic beads coated with GBS antibody are provided in the sample processing solution. A binding solution containing a biotin-labeled GBS antibody is provided in the antibody binding detection section. A color substrate solution containing streptavidine-phycoerythrin (SA-PE) is provided in the luminescent substrate binding section. A termination solution is provided in the termination section, and the termination section may be connected to a spare section as well.

The sample processing solution has the following components:

| NaCl | 138 mM |
|---|---|
| KCl | 2.7 mM |
| BSA | 1% by mass |
| ddH$_2$O | Solvent |

The submicron superparamagnetic immunomagnetic beads have a diameter of 0.5-10 μm and a concentration of 50-200 mg/ml in the sample processing solution.

The first washing sections, the second washing sections, and the third washing sections are provided with washing solutions, and the washing solutions has the following components:

| NaCl | 138 mM |
|---|---|
| KCl | 2.7 mM |
| ddH$_2$O | Solvent |

The binding solution has the following components:

| NaCl | 138 mM |
|---|---|
| KCl | 2.7 mM |
| BSA | 1% by mass |
| Biotin-labeled GBS antibody | 4 μg/ml |
| ddH$_2$O | Solvent |

The color substrate solution has the following components:

| NaCl | 138 mM |
|---|---|
| KCl | 2.7 mM |
| BSA | 1% by mass |
| SA-PE | 4 μg/ml |
| ddH$_2$O | Solvent |

The termination solution has the following components:

| NaCl | 138 mM |
|---|---|
| KCl | 2.7 mM |
| BSA | 1% by mass |
| ddH$_2$O | Solvent |

The working principle of the above GBS kit:

1) The sample is put into the box body, and the flip lid is covered. Then, the box body is inserted into the kit holding tank of the gene detection device. An occulting bar is provided inside the kit holding tank. During the insertion process, the ejector rods of the plungers are sequentially pushed by the occulting bar, so that each plunger 3 is moved against an elastic force of the spring 7, causing the plunger hole to be aligned with the separation cavity, thereby making the various section interconnected.

2) Then, the metal stirrer is driven by the electromagnetic coil array, and the sample is evenly mixed. The GBS antigen in the sample is bound with the GBS antibody on the submicron superparamagnetic immunomagnetic beads (hereinafter referred to as a carrier).

3) The carrier passes through the first washing sections to elute impurities.

4) The carrier enters the antibody binding detection section, and the biotin-labeled GBS antibody is bound to the GBS antigen on the carrier.

5) The carrier passes through the second washing sections to elute the unbound biotin-labeled GBS antibody.

6) The carrier enters the luminescent substrate binding section, and the streptavidin of the luminescent substrate (SA-PE) is specifically bound to the biotin on the carrier.

7) The carrier passes through the third washing sections to elute the unbound luminescent substrate.

8) The carrier enters the termination solution, and the phycoerythrin, i.e., the luminescent substrate on the carrier, generates stable excited light under the excitation light of the instrument.

9) The external device makes use of an optical detection probe to obtain a fluorescence intensity signal from the transparent window of the termination section, and the fluorescence intensity signal is used to qualitatively or quantitatively measure the GBS antigen in the sample.

What is claimed is:
1. A gene detection method, comprising:
1) providing a plurality of separation cavities on a gene detection kit, using at least two plungers to separate adjacent separation cavities, and respectively providing a lysate solution, a washing solution and a reaction solution in the separation cavities;

wherein the gene detection kit comprises a box body with a flip lid at a top, wherein a lysing section, a washing section, and a reaction section separated by the at least two plungers are respectively provided in the box body from top to bottom, the at least two plungers are provided horizontally, and a plunger hole in a vertical direction is provided in each of the at least two plungers; the lysing section is provided with the lysing solution, and the lysing solution is internally provided with ferromagnetic mixing balls and magnetic beads capable of passing through the plunger hole in each of the at least two plungers; the washing section is provided with the washing solution; and the reaction section is provided with the reaction solution;

2) pushing each of the at least two plungers to align the plunger hole of each of the at least two plungers with the adjacent separation cavities, thereby making the plurality of separation cavities interconnected;

3) controlling the magnetic beads in the gene detection kit to drive a sample to be tested to pass through the plurality of separation cavities in sequence by an electromagnetic control method, and carrying out a lysing, a washing, and a reaction in the sequence; and 4) performing an optical detection on a gene in the reaction solution;

wherein the reaction is a polymerase chain reaction (PCR) or an isothermal amplification reaction, wherein an enzyme required for the reaction is provided in the plunger hole of the plunger between the washing section and the reaction section, and when the plunger hole of the plunger between the washing section and the reaction section is aligned with the reaction section containing the reaction solution, the enzyme automatically falls into the reaction solution due to a gravity of the enzyme.

2. The gene detection method of claim 1, wherein a detection portion of the optical detection is located at a bottom of the separation cavity containing the reaction solution, and the bottom of the separation cavity containing the reaction solution is provided with a concave portion toward an outside of the gene detection kit;

during a detection, the gene detection kit is in an inclined state, and the concave portion of the separation cavity containing the reaction solution faces downward, and the magnetic beads in the reaction solution are automatically concealed in the concave portion to avoid an interference on the optical detection.

\* \* \* \* \*